(12) United States Patent
Lyons et al.

(10) Patent No.: US 8,343,949 B2
(45) Date of Patent: Jan. 1, 2013

(54) STABILIZED COMPOSITIONS COMPRISING A THERAPEUTICALLY ACTIVE AGENT, AND AN OXIDIZING PRESERVATIVE

(75) Inventors: Robert T. Lyons, Laguna Hills, CA (US); Robert S. Jordan, Trabuco Canyon, CA (US)

(73) Assignee: Allergan, Inc., Irvine, CA (US)

( * ) Notice: Subject to any disclaimer, the term of this patent is extended or adjusted under 35 U.S.C. 154(b) by 711 days.

(21) Appl. No.: 11/570,200

(22) PCT Filed: May 19, 2005

(86) PCT No.: PCT/US2005/018026
§ 371 (c)(1),
(2), (4) Date: Dec. 7, 2006

(87) PCT Pub. No.: WO2005/123135
PCT Pub. Date: Dec. 29, 2005

(65) Prior Publication Data
US 2008/0300315 A1      Dec. 4, 2008

(51) Int. Cl.
*A61K 31/33*      (2006.01)
(52) U.S. Cl. ........................................ 514/183
(58) Field of Classification Search .................... 514/183
See application file for complete search history.

(56) References Cited

U.S. PATENT DOCUMENTS

| | | | |
|---|---|---|---|
| 2,988,514 A | 6/1961 | Robson et al. | |
| 3,278,447 A | 10/1966 | McNicholas | |
| 4,689,215 A | 8/1987 | Ratcliff | |
| 4,696,811 A | 9/1987 | Ratcliff | |
| 5,246,662 A | 9/1993 | Ripley et al. | |
| 5,279,673 A | 1/1994 | Dziabo et al. | |
| 5,424,078 A | 6/1995 | Dziabo et al. | |
| 5,538,974 A * | 7/1996 | Ogawa et al. | 514/252.13 |
| 5,736,165 A | 4/1998 | Ripley et al. | |
| 2002/0035264 A1 | 3/2002 | Kararli et al. | |
| 2002/0193441 A1* | 12/2002 | Robertson | 514/573 |
| 2003/0203034 A1* | 10/2003 | Huth | 424/487 |

FOREIGN PATENT DOCUMENTS

| | | |
|---|---|---|
| CA | 2004097 | 5/1990 |
| CA | 2003198 | 3/1995 |
| EP | 0 347 320 | 12/1989 |
| EP | 0 371 728 | 6/1990 |
| WO | WO90/06126 | 6/1990 |
| WO | WO96/02264 A2 | 2/1996 |

OTHER PUBLICATIONS

Schriver, Atkins, Langford, Inorganic Chemistry, New York: W.H. Freeman and Company, 1990, pp. 649 and 654.

* cited by examiner

*Primary Examiner* — Brandon Fetterolf
*Assistant Examiner* — Christopher R Stone
(74) *Attorney, Agent, or Firm* — Kevin J. Forrestal

(57) ABSTRACT

Citric acid and conjugate bases thereof are useful for stabilizing stabilized chlorine dioxide in the presence of therapeutically active agents and excipients in a composition. Ophthalmic compositions and methods related thereto are also disclosed herein.

2 Claims, 2 Drawing Sheets

STABILIZED COMPOSITIONS COMPRISING A THERAPEUTICALLY ACTIVE AGENT, AND AN OXIDIZING PRESERVATIVE

CROSS REFERENCE TO RELATED APPLICATIONS

This is a national stage application under 35 U.S.C. §371 of PCT application PCT/US 2005/018026, filed on May 19, 2005, which claims the benefit of Nonprovisional application Ser. No. 10/865,639, filed on Jun. 9, 2004.

FIELD OF THE INVENTION

The present invention relates to pharmaceutical compositions. In particular, the present invention relates to ophthalmic compositions containing an active drug and the use of stabilized chlorine dioxide as a preservative in these compositions.

BACKGROUND OF THE INVENTION

Description of Related Art

Preservatives are used in multi-use ophthalmic formulations to prevent microbial contamination of the composition after the packaging has been opened. A number of preservatives have been used including quaternary ammonium salts such as benzalkonium chloride; mercury compounds such as phenylmercuric acetate and thimerosal; alcohols such as chlorobutanol and benzyl alcohol; and others. Recently, stabilized chlorine dioxide has also been disclosed as being useful as a preservative in ophthalmic compositions, see for example, U.S. Pat. No. 5,736,165; U.S. Pat. No. 5,424,078; and WO 9602264A2; all of which are expressly incorporated herein by reference.

At least one commercial ophthalmic product, Alphagan P®, marketed by Allergan, Inc., the assignee of the present patent document uses stabilized chlorine dioxide as a preservative. The active agent of Alphagan P® is brimonidine, an alpha 2-adrenoceptor agonist, and the product is used for the treatment of glaucoma and other conditions associated with elevated intraocular pressure.

SUMMARY OF THE INVENTION

One embodiment comprises an ophthalmic composition comprising an effective amount of a therapeutically active agent, stabilized chlorine dioxide, and citric acid and/or conjugate bases thereof.

A method of stabilizing incompatible components of a composition comprising adding an effective amount of citric acid and/or conjugate bases thereof, wherein said incompatible components comprise stabilized chlorine dioxide and a second component, is also disclosed herein.

Another embodiment comprises a method of preserving an ophthalmic composition comprising providing an effective amount of citric acid and/or conjugate bases thereof and stabilized chlorine dioxide to said composition.

BRIEF DESCRIPTION OF THE DRAWING FIGURES

DETAILED DESCRIPTION OF THE INVENTION

Figure 1:
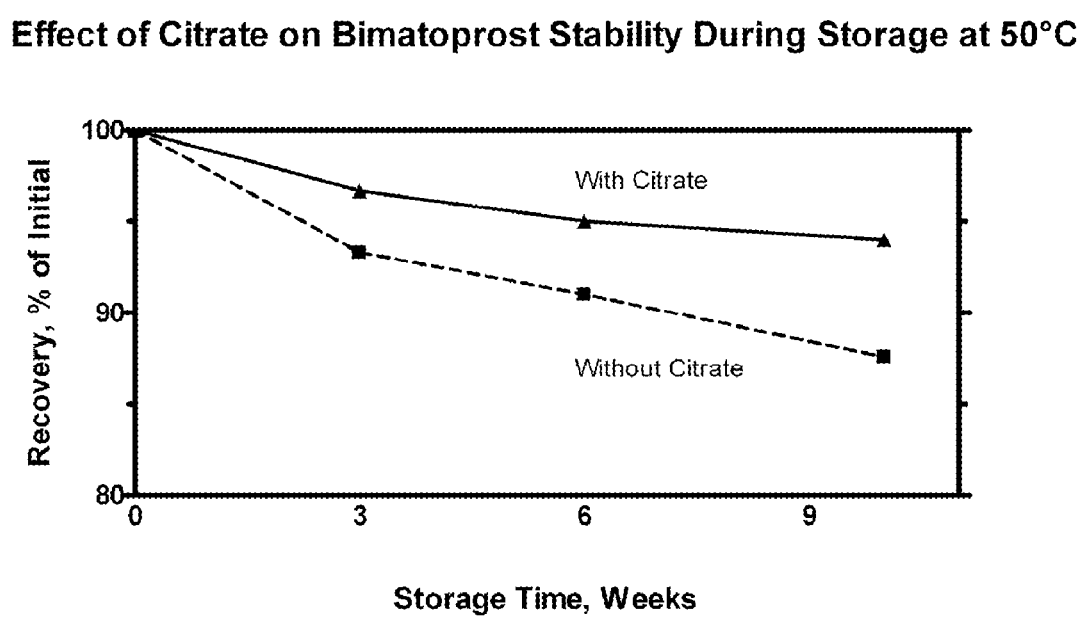
FIG. 1 shows the effect of citrate on bimatoprost stability in the composition of Table 4 at 50° C.

We have found many therapeutically active agents and some other components of many ophthalmic compositions are incompatible with stabilized chlorine dioxide, which is a useful preservative for ophthalmic compositions. Particularly, stabilized chlorine dioxide and therapeutically active agents or other components of an ophthalmic formulation are unstable in one another's presence. In other words, if stabilized chlorine dioxide is in a composition with certain therapeutically active agents, either the stabilized chlorine dioxide, or the therapeutically active agent, or both, are unstable. Similarly, if stabilized chlorine dioxide is in a composition with certain other excipients, either the stabilized chlorine dioxide, or the other excipient, or both, are unstable. Surprisingly, citric acid and/or conjugate bases thereof have been discovered to improve the stability of these combinations.

As used herein, the term "therapeutically active agent" is understood in the broadest sense generally accepted in the art to be a compound or compounds which are used to treat or prevent any disease or undesirable condition which afflicts an animal.

The term "stabilized chlorine dioxide" is well known in the industry and by those skilled in the art. The term "stabilized chlorine dioxide" as used herein means, for example, one or more chlorine dioxide-containing complexes disclosed in U.S. Pat. Nos. 4,696,811 and 4,689,215, which are incorporated herein by reference. Chlorites include metal chlorite salts, particularly alkali metal chlorites. A specific example of a chlorite salt which is useful as a chlorine dioxide precursor is sodium chlorite. Among the preferred stabilized chlorine dioxide complexes are carbonate and bicarbonate complexes. The exact chemical composition of many of these stabilized chlorine dioxide precursors is not completely understood. The manufacture or production of certain chlorine dioxide precursors is described in McNicholas U.S. Pat. No. 3,278,447, which is hereby incorporated in its entirety by reference herein. A commercially available stabilized chlorine dioxide which can be utilized in the compositions disclosed herein is the proprietary stabilized chlorine dioxide of BioCide International, Inc. of Norman, Okla., sold under the trademark Purite®. Other suitable stabilized chlorine dioxide products include that sold under the trademark Dura Klor® by Rio Linda Chemical Company, Inc., and that sold under the trademark Antheium Dioxide® by International Dioxide, Inc. The amount of stabilized chlorine dioxide used depends upon the therapeutically active agent, other excipients, and other aspects of the formulation process. Such a determination can readily be made by a person of ordinary skill in the art, without undue experimentation. While the amount of stabilized chlorine dioxide may vary widely, a concentration between 30 ppm and 500 ppm is useful in many compositions. In other compositions, from 50 ppm and 150 ppm stabilized chlorine dioxide is used.

The term "citric acid and/or conjugate bases thereof" refers to citric acid and its monovalent (−1), divalent (−2), and trivalent (−3) salts in any combination. Thus, any one of these species and any combination thereof is considered to be within the meaning of the phrase "citric acid and/or conjugate bases thereof". The concentration of citric acid in the compositions disclosed herein may vary. In some compositions, the concentration of citric acid and/or conjugate bases thereof is from 0.001% to 0.10%. In other compositions, the concentration of citric acid and/or conjugate bases thereof is about 0.02%. Unless a specific amount of a specific form is indicated, the concentration of citric acid and/or conjugate bases thereof is determined as if all citric acid and citrate species were citric acid.

U.S. Pat. No. 5,246,662 teaches that transition metals are capable of catalyzing the conversion of stabilized chlorine dioxide to the active form. Thus, while not intending to be limited or bound in any way by theory as to the scope of the present invention, it is believed that trace transition metals help to accelerate the formation of active chlorine dioxide, which in turn oxidizes the therapeutically active agent or an excipient. Thus, it is believed that citric acid acts as a chelating agent to bind up these trace metals, stabilizing the incompatible components in each others' presence. While the trace metals are not deliberately added, it is believed that sufficient quantities of these metals are present in common ophthalmic excipients to effect the freeing of chlorine dioxide. Furthermore, while not intending to be bound in any way by theory, it is believed that the citric acid enhances the preservative effectiveness because binding the metal deprives microbial contaminants of nutrients, thus inhibiting their growth, and/or helping to kill the pathogen.

While not intending to be bound in any way by theory, it is believed that polyanions such as carboxymethylcellulose (CMC) have a sufficient quantity of transition metal impurities to overcome the chelating properties of these compounds, such that they do not stabilize the incompatible components, but can actually destabilize them. It is believed that this is because polymeric materials are much more difficult to purify than small molecules, due to the fact that these materials generally constitute a mixture, and are not a pure, single compound. It is believed that this is the reason that carboxymethylcellulose was observed to destabilize certain incompatible components. By contrast citric acid is believed to be sufficiently pure to stabilize the incompatible components contemplated herein.

While not intending to be bound in any way by theory, it is also believed that many chelating agents have oxidizable groups which make them unsuitable for stabilizing chlorine dioxide. For example, amines with amine functional groups such as EDTA and ethylene diamine are oxidized by the stabilized chlorine dioxide, and are thus not suitable chelating agents for the purposes disclosed herein.

While not intending to be bound in any way by theory, other potential chelating agents such as lactate, pyruvate, and oxalate, are believed to either be too weak as metal chelating agents to be effective, or susceptible to oxidation, or both, such that they do not appear to stabilize the incompatible components of a composition.

In one embodiment, the therapeutically active agent of the compositions disclosed herein is bimatoprost which is a prostamide compound. While not intending to be bound in any way by theory, it is generally believed in the art that oxidation reactions are generally nonselective reactions, the fact that stabilized chlorine dioxide destabilizes bimatoprost suggests that a broad variety of compounds will be oxidized by chlorine dioxide. Furthermore, chlorine dioxide is a strong oxidant (as evidenced by the fact that we are using "stabilized" chorine dioxide), and would thus be even less selective than a "normal" oxidant. For comparison, the standard reduction potential of chlorine dioxide to $ClO_2^-$ is 1.07 V, whereas the standard reduction potential of permanganate to manganese dioxide is 0.6 V [Schriver, Atkins, Langford, Inorganic Chemistry, New York: W.H. Freeman and Company, 1990, pp. 649 and 654]. Permanganate has been used as a reagent for many oxidations in organic chemistry including the oxidative cleavage of alkenes to ketones or carboxylic acids, the oxidative cleavage of ketones to carboxylic acids, the oxidation of alcohols or aldehydes to carboxylic acids, and various oxidations of amine and sulfur containing functional groups. Thus, while not intending to be bound in any way by theory, chlorine dioxide, being a stronger oxidizing agent than permanganate, is expected to oxidize many functional groups.

In one embodiment, the therapeutically active agent comprises a carboxylic acid, a carboxylic acid ester, or a carboxylic acid amide. In another embodiment, the therapeutically active agent is a prostaglandin or prostamide such as bimatoprost, latanoprost, travoprost, unoprostone isopropyl, and the like, which have carboxylic acid, ester, or amide groups. In another embodiment, the therapeutically active agent comprises a sulfur atom. Other functional groups that may be susceptible to stabilized chlorine dioxide are amines, phenols, alcohols, aromatic amino acids, non-conjugated double bonds, and similar groups. While not intending to be limiting, or to be bound by theory, non-active excipients comprising one or more of the aforementioned functional groups should be stabilized by citric acid such that they can be used with stabilized chlorine dioxide.

As is known in the art, buffers are commonly used to adjust the pH to a desirable range for ophthalmic use. Generally, a pH of around 6-8 is desired, however, this may need to be adjusted due to considerations such as the stability or solubility of the therapeutically active agent or other excipients. Many buffers including salts of inorganic acids such as phosphate, borate, and sulfate are known. Although any buffer may be used in the compositions disclosed herein, in certain situations it is particularly useful to use a borate/boric acid buffer in the compositions disclosed herein. The term "borate/boric acid buffer" refers to any combination of boric acid and one or more of the conjugate bases such that the pH is adjusted to the desired range. While not intending to limit the scope of the invention in any way, or be bound in any way by theory, it is believed that the borate/boric acid buffer may boost the antimicrobial properties of stabilized chlorine dioxide.

In another embodiment, the therapeutically active agent is a prostaglandin or a prostamide. In another embodiment, the therapeutically active agent is bimatoprost. One composition comprises from 0.01% to 0.10% bimatoprost. In another embodiment, the concentration of bimatoprost is about 0.03%.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

Another composition comprises 0.03% bimatoprost, 0.39% sodium chloride, 0.6% boric acid, 0.045% sodium borate decahydrate, 0.014% citric acid monohydrate, 0.5% carboxymethylcellulose, and 0.005% Purite® (stabilized chlorine dioxide), wherein the pH is adjusted to 7.3 by the addition of hydrochloric acid (HCl) or sodium hydroxide (NaOH).

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

The best mode of making and using the present invention are described in the following examples. These examples are given only to provide direction and guidance in how to make and use the invention, and are not intended to limit the scope of the invention in any way.

EXAMPLE 1

The following example is typical of the instability of various common ophthalmic excipients in the presence of stabilized chlorine dioxide. Each of the excipients was added, in the amounts shown, to a proprietary composition comprising brimonidine as a therapeutically active agent. The results, presented in Table 1, show that none of the excipients appear to stabilize the chlorine dioxide. In particular, EDTA and ethylene diamine, which are known chelating agents, do not stabilize the chlorine dioxide. Also of note is that some of the other compounds that might be viewed as chelating agents, such as oxalate or pyruvate, are similarly ineffective.

TABLE 1

Effect of Chelating Agents on Stability of Chlorine Dioxide

| Ingredient (ppm) | pH | Stabilized Chlorine Dioxide Concentration (ppm) | | |
|---|---|---|---|---|
| | | 0 Days | 7 Days | 14 Days |
| None (control) | 7.3 | 42 | 41 | 38 |
| Sodium Formate (100) | 7.3 | 42 | 40 | 36 |
| Sodium Lactate (100) | 7.3 | 45 | 40 | 37 |
| Sodium Pyruvate (100) | 7.3 | 41 | 15 | 0 |
| Sodium Dihydroxyfurmarate (100) | 7.1 | 37 | 13 | 0 |
| Sodium Oxalate (100) | 7.3 | 39 | 38 | 35 |
| Ethylene diamine (100) | 7.2 | 42 | 37 | 29 |
| EDTA (100) | 7.2 | 44 | 2 | 0 |
| Sodium Oxalate (100) + Fe(III) (1) | 7.3 | 43 | 38 | 39 |
| Ethylene oxide (100) | 7.3 | 43 | 40 | 35 |
| Acetone (100) | 7.3 | 43 | 38 | 35 |
| Glucose (100) | 7.3 | 43 | 41 | 34 |

EXAMPLE 2

Compositions A, B, and C were prepared according to Table 2. All compositions were prepared in a similar manner. A composition is manufactured on a volume basis at ambient temperatures from two principal parts designated I and II. Each in-process part is prepared separately and then combined. The resulting bulk composition is pH adjusted and then brought to volume for final mix.

Part I is manufactured in the main batch vessel. Water is charged to the main mixing vessel at 50% of the final batch volume. Mixing is initiated at a specified speed using a Rotosolver mixer positioned off-center to produce a strong vortex, and CMC is added directly into the vortex. The solution is mixed for a specified time until complete dissolution is achieved.

Part II is manufactured in a separate mixing vessel equipped with a top-entering variable-speed mixer and an appropriately sized impeller. Water is charged to the tank at 35% of the batch volume ad mixing is initiated at a specified speed. The ingredients for Part II are added in the following order: boric acid, sodium borate, sodium chloride, bimatoprost, and Purite®. Each ingredient is allowed to completely dissolve before the next ingredient is added.

With continued mixing in the main batch vessel, Part II is quantitatively transferred into Part I. The combined parts are mixed for a specified time to ensure homogeneity. The pH is measured and adjusted to pH 7.3 with NaOH and/or HCl. Water is added to final volume and the bulk solution is mixed until homogeneous. The osmolality of the final solution is about 290 mOsm/kg.

The samples were held at 50° C. for 13 weeks and the concentration of bimatoprost was determined by high performance liquid chromatography. The concentration of Purite® was determined by titration and is reported as potential chlorine dioxide (CDO) concentration in ppm. The Purite® analysis procedure is based on the reduction of chlorite ion by iodide in acidic medium. The liberated iodine is then back-titrated using sodium thiosulfate to calculate the amount of sodium chlorite. Results are reported as potential chlorine dioxide rather than in terms of sodium chlorite (or Purite®) because CDO is the active form of the preservative While not intending to limit the scope of the invention in any way, the results, presented in Table 3, demonstrate that the addition of low viscosity carboxymethylcellulose polymer (CMC), with or without NaCl, tends to destabilize both the bimatoprost and the Purite®.

TABLE 2

Base Composition Comprising Bimatoprost and Purite ®.

| | Concentration (% w/w) | | |
|---|---|---|---|
| Ingredient | A | B | C |
| Bimatoprost | 0.03 | 0.03 | 0.03 |
| Purite | 0.015 | 0.015 | 0.015 |
| Boric Acid | 0.60 | 0.60 | 0.60 |
| Sodium Borate | 0.045 | 0.045 | 0.045 |
| Sodium Chloride | 0 | 0 | 0.39 |
| Carboxymethylcellulose | 0 | 0.50 | 0.50 |
| HCl/NaOH | pH to 7.3 | pH to 7.3 | pH to 7.3 |
| Purified Water | q.s. 100% | q.s. 100% | q.s. 100% |

TABLE 3

Bimatoprost and Purite ® Content in Formulations of Table 2 After 13 Weeks at 50° C.

| Composition | Bimatoprost, % of Initial | Purite ®, % of Initial |
|---|---|---|
| Borate Buffer (A) | 91.0 | 100.5 |
| Borate + CMC (B) | 84.5 | 95.7 |
| Borate + CMC + NaCl (C) | 82.2 | 96.0 |

EXAMPLE 3

Figure 2:
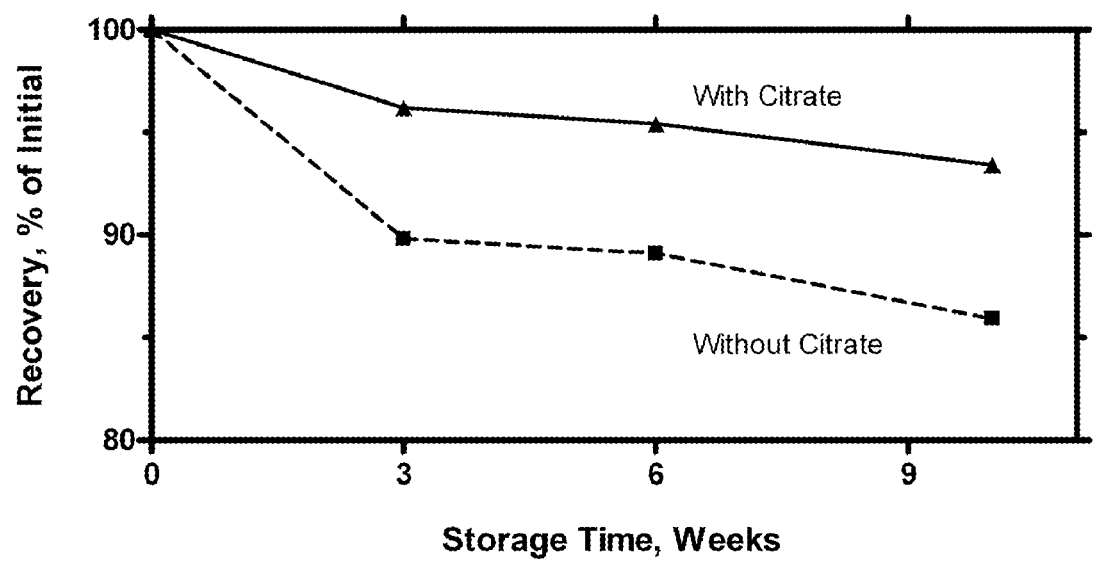
FIG. 2 shows the effect of citrate on Purite® stability in the composition of Table 4 at 50° C.

Compositions D and E were prepared according to Table 4 by a procedure similar to that described in Example 2. Citric acid was added after the dissolution of sodium chloride and the pH was measured and adjusted to pH 7.3 with NaOH and/or HCl before the addition of bimatoprost and Purite®. The samples were stored at 50° C. and the concentrations of bimatoprost (FIG. 1) and Purite® (FIG. 2) were determined at 3, 6 and 10 weeks. While not intending to limit the scope of the invention in any way, FIGS. 1 and 2 demonstrate that citrate stabilizes both bimatoprost and Purite® in the composition.

TABLE 4

Composition of Bimatoprost With and Without Citric Acid

| Ingredient | Concentration (% w/w) | |
| --- | --- | --- |
| | D | E |
| Bimatoprost | 0.03 | 0.03 |
| Purite ® | 0.005 | 0.005 |
| Citric Acid | 0.014 | — |
| Boric Acid | 0.60 | 0.60 |
| Sodium Borate | 0.045 | 0.045 |
| Sodium Chloride | 0.39 | 0.39 |
| Carboxymethylcellulose | 0.50 | 0.50 |
| HCl/NaOH | pH to 7.3 | pH to 7.3 |
| Purified Water | q.s. 100% | q.s. 100% |

EXAMPLE 4

A composition, prepared according to Table 5, was entirely manufactured in a single batch vessel and was prepared as follows. The ingredients are added into purified water with mixing in the following order: sodium phosphate dibasic heptahydrate, citric acid monohydrate, sodium chloride, bimatoprost, and Purite®. Each ingredient was allowed to dissolve completely before the next ingredient was added. The pH was then measured and adjusted to 7.3, and purified water was added to bring the composition to final volume. After storage for six months at 40° C., 99.7% of initial bimatoprost and 99.6% of initial Purite® remained in the product. While not intending to limit the scope of the invention in any way, these data demonstrate that the citrate provides excellent storage stability for bimatoprost and Purite®.

TABLE 5

Composition of Bimatoprost in Phosphate/Citrate Buffer

| Ingredient | Concentration (% w/w) E |
| --- | --- |
| Bimatoprost | 0.03 |
| Purite ® | 0.01 |
| Sodium Phosphate Dibasic | 0.268 |
| Citric Acid | 0.014 |
| Sodium Chloride | 0.83 |
| HCl/NaOH | pH to 7.3 |
| Purified Water | q.s. 100% |

EXAMPLE 5

A composition according to example 4 is administered topically once a day to the eyes of a patient suffering from glaucoma. Reduction of the patient's intraocular pressure is observed shortly after administration, and continues for as long as the composition is administered.

What is claimed is:

1. An ophthalmic composition consisting of:
(a) about 0.03% bimatoprost;
(b) about 0.005% Purite®;
(c) about 0.014% citric acid;
(d) about 0.60% boric acid;
(e) about 0.045% sodium borate;
(f) about 0.39% sodium chloride;
(g) about 0.5% carboxymethylcellulose,
(h) HCl/NaOH and
(i) purified water.

2. An ophthalmic composition consisting of:
(a) about 0.03% bimatoprost;
(b) about 0.01% Purite®;
(c) about 0.268 sodium phosphate dibasic;
(d) about 0.014% citric acid;
(e) about 0.83% sodium chloride;
(f) HCl/NaOH; and
(q) purified water.

* * * * *